(12) United States Patent
Sadek et al.

(10) Patent No.: US 6,606,995 B1
(45) Date of Patent: Aug. 19, 2003

(54) STENTS FOR CHOANAL ATRESIA

(76) Inventors: Sarwat Abdel Aziz Sadek, Consultant ENT Surgeon, Musgrove Park Hospital, Musgrove Park, Taunton Somerset (GB), TA1 5DA; Akram Sarwat Sadek, 162 Cheviot Gardens, London (GB), NW2 1QA ( * ) Notice: Subject to any disclaimer, the term of this patent is extended or adjusted under 35 U.S.C. 154(b) by 0 days.

(21) Appl. No.: 10/030,926

(22) PCT Filed: Jul. 31, 2000

(86) PCT No.: PCT/GB00/02934

§ 371 (c)(1),
(2), (4) Date: Apr. 19, 2002

(87) PCT Pub. No.: WO01/12111

PCT Pub. Date: Feb. 22, 2001

(30) Foreign Application Priority Data

Aug. 11, 1999 (GB) ............................................. 9918973

(51) Int. Cl.⁷ ............................................. A61M 15/08
(52) U.S. Cl. ............................... 128/207.18; 128/207.14
(58) Field of Search ...................... 128/200.24, 200.26, 128/206.11, 207.14, 207.15, 207.18, 203.18; 606/108; 604/106, 19

(56) References Cited

U.S. PATENT DOCUMENTS

| | | | | |
|---|---|---|---|---|
| 3,814,103 A | * | 6/1974 | Fettel et al. | 128/207.18 |
| 4,185,639 A | * | 1/1980 | Linder | 128/200.26 |
| 5,185,005 A | * | 2/1993 | Ballantyne | 604/174 |
| 5,601,594 A | * | 2/1997 | Best | 606/199 |

FOREIGN PATENT DOCUMENTS

| | | | | |
|---|---|---|---|---|
| DE | 29607589 U1 | * | 8/1996 | A61F/5/08 |
| GB | 2307412 A | * | 5/1997 | A61L/29/00 |
| SU | 1512617 A1 | * | 7/1987 | |

OTHER PUBLICATIONS

Sadek, S.A.A., Congenital Bilateral Choanal Atresia, International Journal of Pediatric Otorhinolaryngology, 42 (1998), 247–256.*

Gundfase, Kenneth M., Thomsen, James R., Barber, Colin S., An Improved Stent Method for Choanal Atresia Repair, Laryngoscope 100, 1132–1133 (Oct. 1990).*

Dunham, Michael E., The Child's Doctor Journal of Children's Memorial Hospital Chicago, Fall 1998.*

* cited by examiner

Primary Examiner—Glenn K. Dawson
Assistant Examiner—Mark Rademacher (57) ABSTRACT

A choanal atresia stent has two curved hollow tubes 1 bridged by a flexible transverse tube 2. It is placed into position by two fine guides 8 that are passed through the nose and brought out the mouth. The clip 7 at the guide end is clipped onto the clip 6 at the tapered end 5 of the stent. The stent is then passed from the mouth through the back of the nose to the front of the nose. Further movement is arrested by the transverse tube 2 at the nasal septum. The stent is secured in place by sliding two short connected tubes 9, 10 onto the two long hollow tubes 1. Fixation is achieved through an adjustable catch mechanism 4. Excess tubing is trimmed off. The stents are removed without general anaesthesia by cutting the thread in one long tube 1 below the level where the thread 3 is fixed.

4 Claims, 8 Drawing Sheets

STENTS FOR CHOANAL ATRESIA

BACKGROUND OF THE INVENTION

This invention relates to stents for choanal atresia.

Choanal atresia is a condition where babies are born without an opening at the back of the nose. The condition is treated by creating an opening for breathing. In order to maintain the openings, stents in the form of hollow tubes are inserted in the nose. Many tubes have been designed by different surgeons, but they are inadequate, traumatic and most importantly unstable.

BRIEF SUMMARY OF THE INVENTION

According to the present invention, there is provided a choanal atresia stent. The stent consists of two hollow tubes bridged together towards one end by a small, flexible transverse tube. The transverse tube is rigidly attached to only one of the long tubes. A strong thread attached to the inner walls of both long tubes threads through the long tubes and the transverse tube, keeping them all rigidly connected together.

The long tubes taper off towards their distal portions to end with clips.

The stent also comprises of two fine, flexible guides, which serve to be passed through the nose and brought out the mouth for attachment to the hollow tubes by the clips. This allows the hollow tubes to be pulled through the nose such that the transverse tube is arrested from further movement by the back of the nose.

Also included are two short hollow tubes rigidly connected by a transverse tube. The inside of the hollow tubes are grooved. The short tubes would slide over the long, hollow tubes for fixation at the nasal end. Fixation is achieved by an adjustable clasp mechanism consisting of concentric raised ridges on the long tubes that engage the grooves on the inside of the short hollow tubes.

This design solves the problem of instability, which may reduce the incidence of restenosis in the newly established airway. The stent is also easily inserted and reduces the length of the surgical procedure by eliminating time spent in fashioning complicated and fiddly stents for every case.

BRIEF DESCRIPTION OF THE SEVERAL VIEWS OF DRAWINGS

A specific embodiment of the invention will now be described by way of example with reference to the accompanying in which.

DETAILED DESCRIPTION OF THE INVENTION

Referring to the drawing, the choanal atresia stent comprises two curved, hollow tubes 1 bridged towards their proximal ends by a flexible transverse tube 2. The transverse tube 2 is rigidly attached to only one of the long tubes 1. The strong thread 3 attached to the inner walls of both long tubes 1, threads through the transverse tube 2 and keeps all three tubes rigidly connected together.

After surgically establishing an opening at the back of the nose, the two fine guides 8 are inserted into the nose such that the clip 7 is inserted first. They are then pushed through the back of the nose and brought out the mouth.

Figure 1:
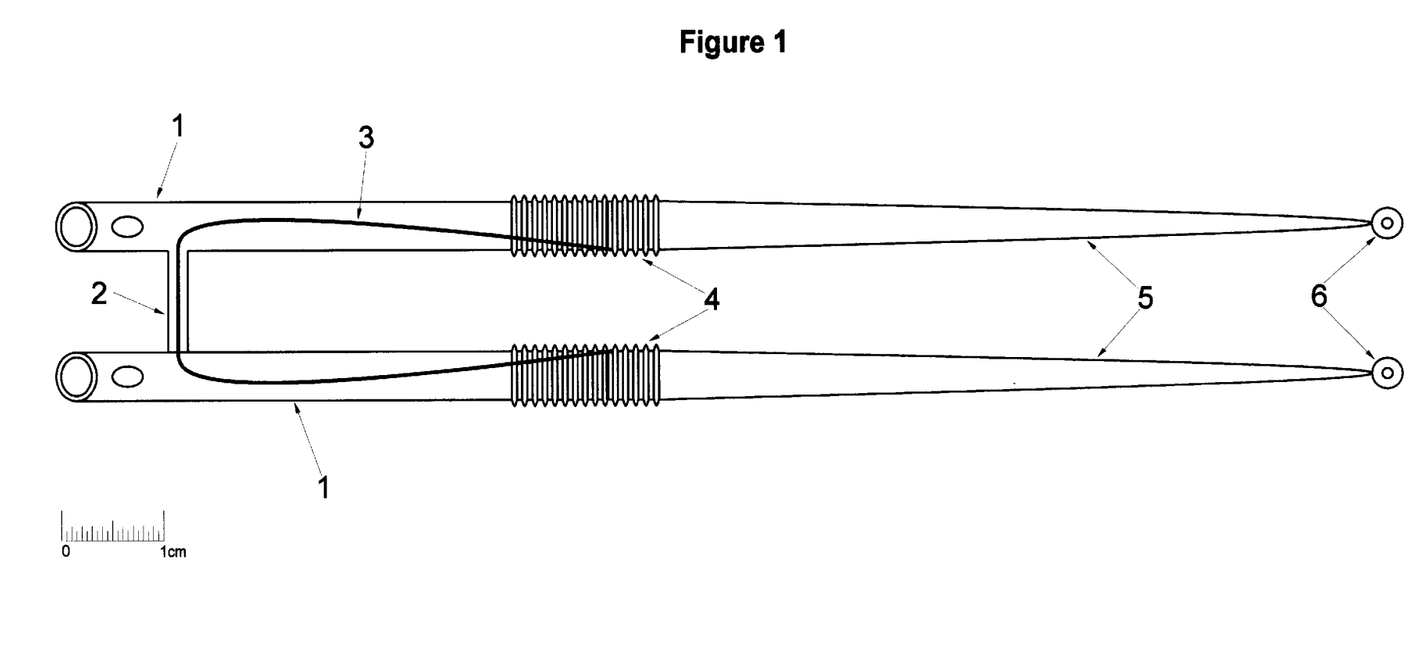
FIG. 1 shows from the top, the long hollow tubes bridged by the flexible, transverse tube rigidly connected together by the strong thread attached to the inner walls.
Figure 2:
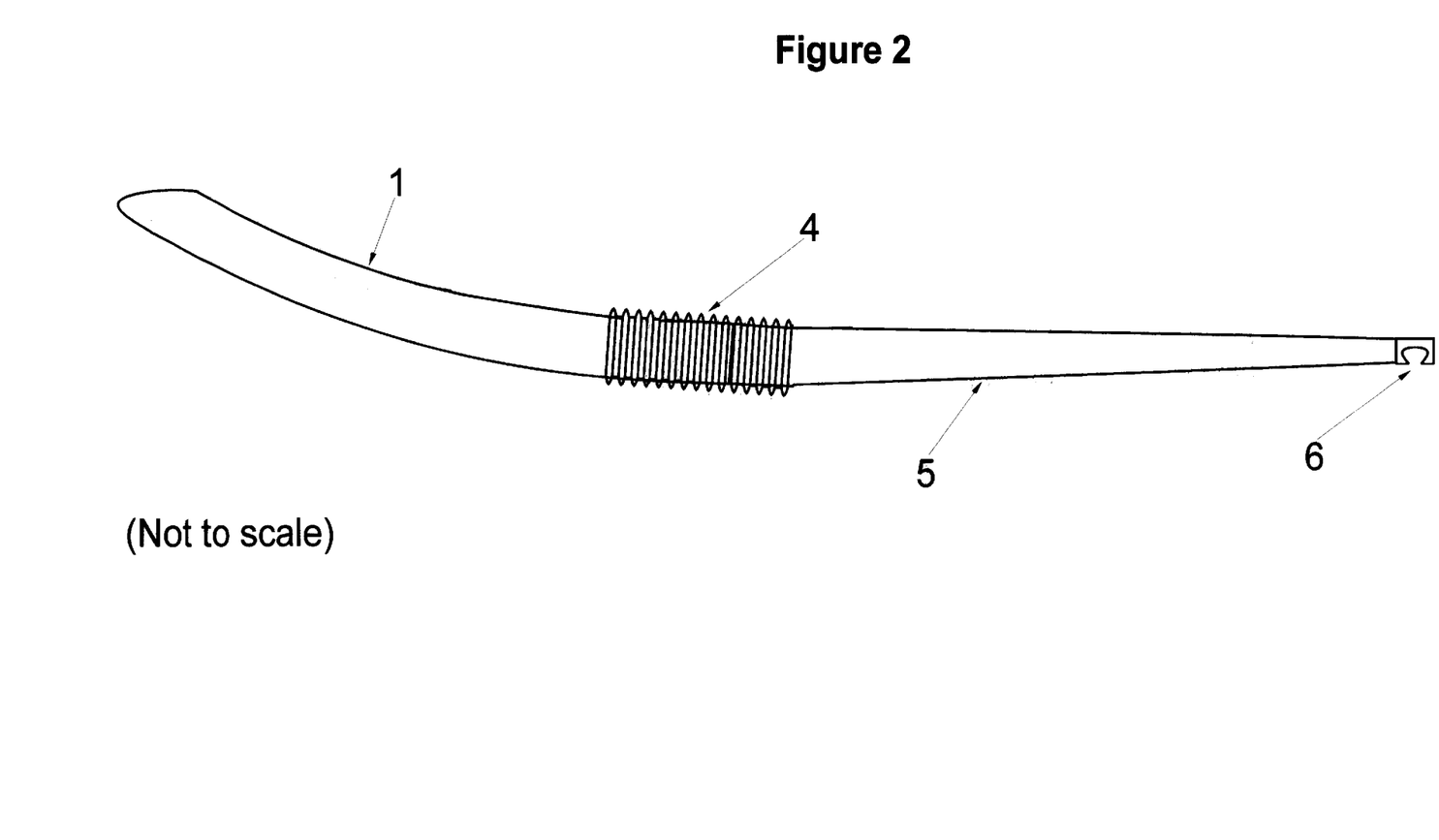
FIG. 2 shows the long hollow tubes from the side illustrating the curvature at the proximal end as well as the concentric raised ridges and clips at the tapered end of the tube.
Figure 3:
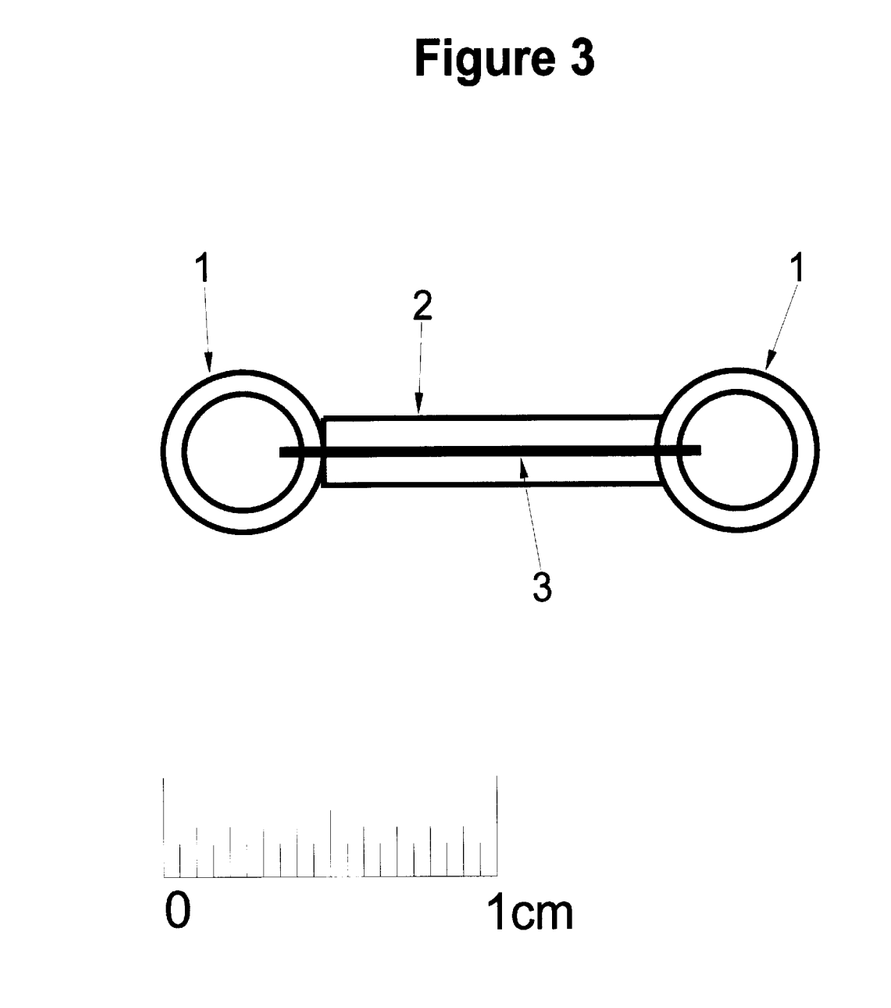
FIG. 3 shows in cross section, the long hollow tubes bridged by the flexible transverse tube rigidly attached to only one of the long tubes with the strong thread within the tube.
Figure 4:
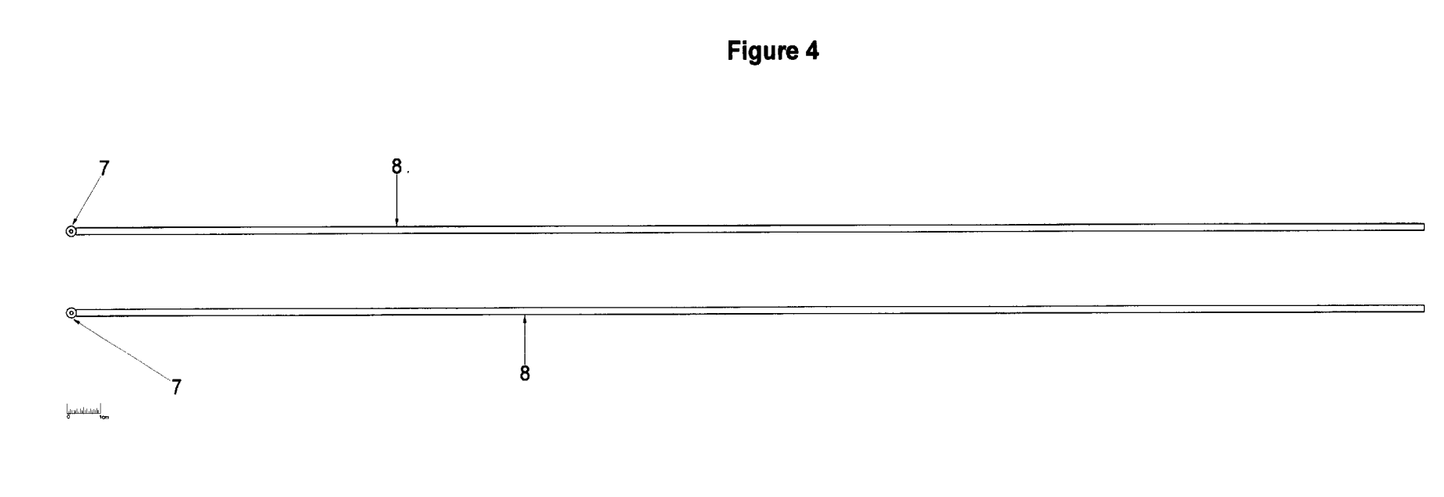
FIG. 4 shows the two fine, flexible guides with clips on the end for attachment to the long hollow tubes.
Figure 5:
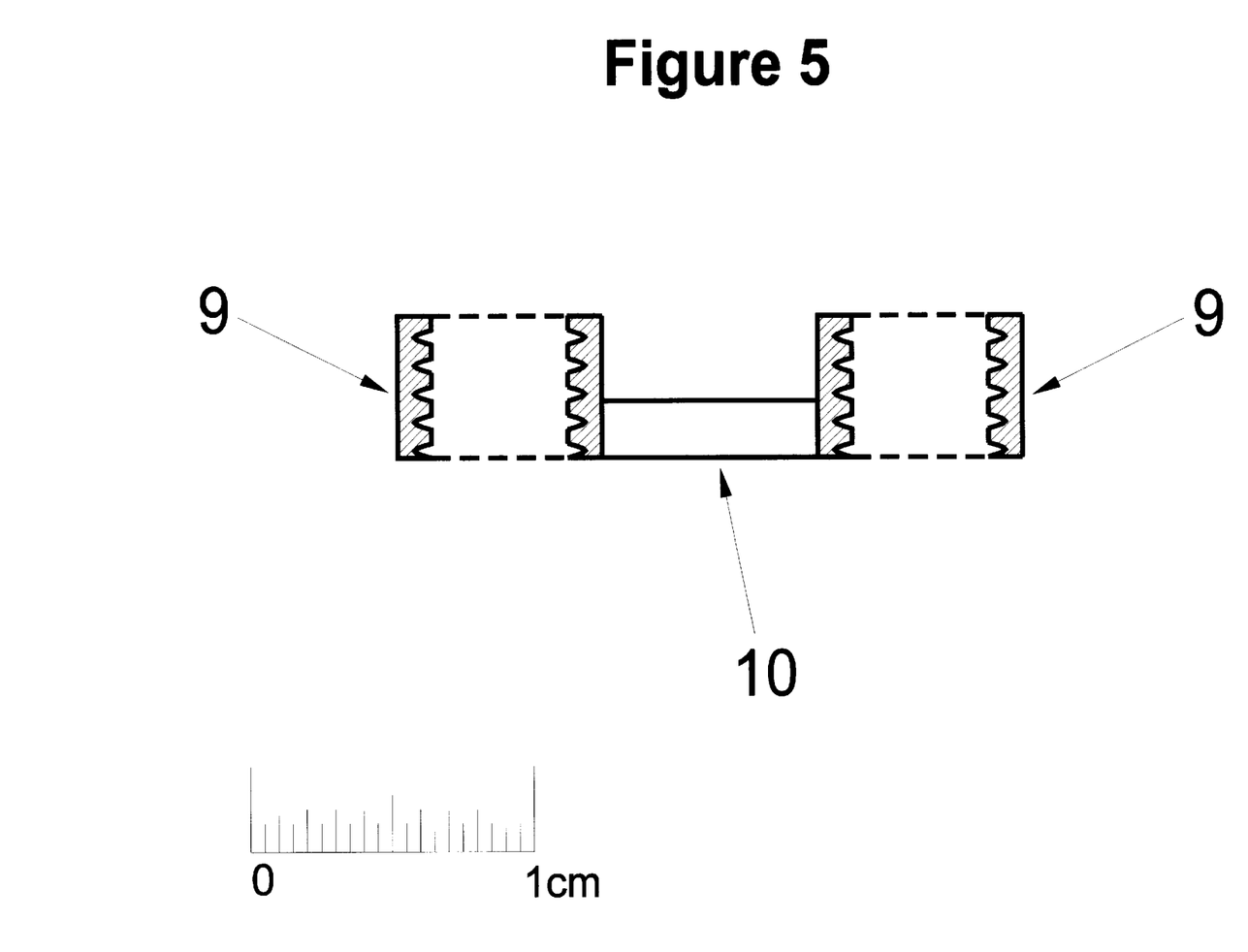
FIG. 5 illustrates in longitudinal section, the short hollow tubes connected by a rigid transverse tube, with concentric grooves on the inside.
Figure 6:
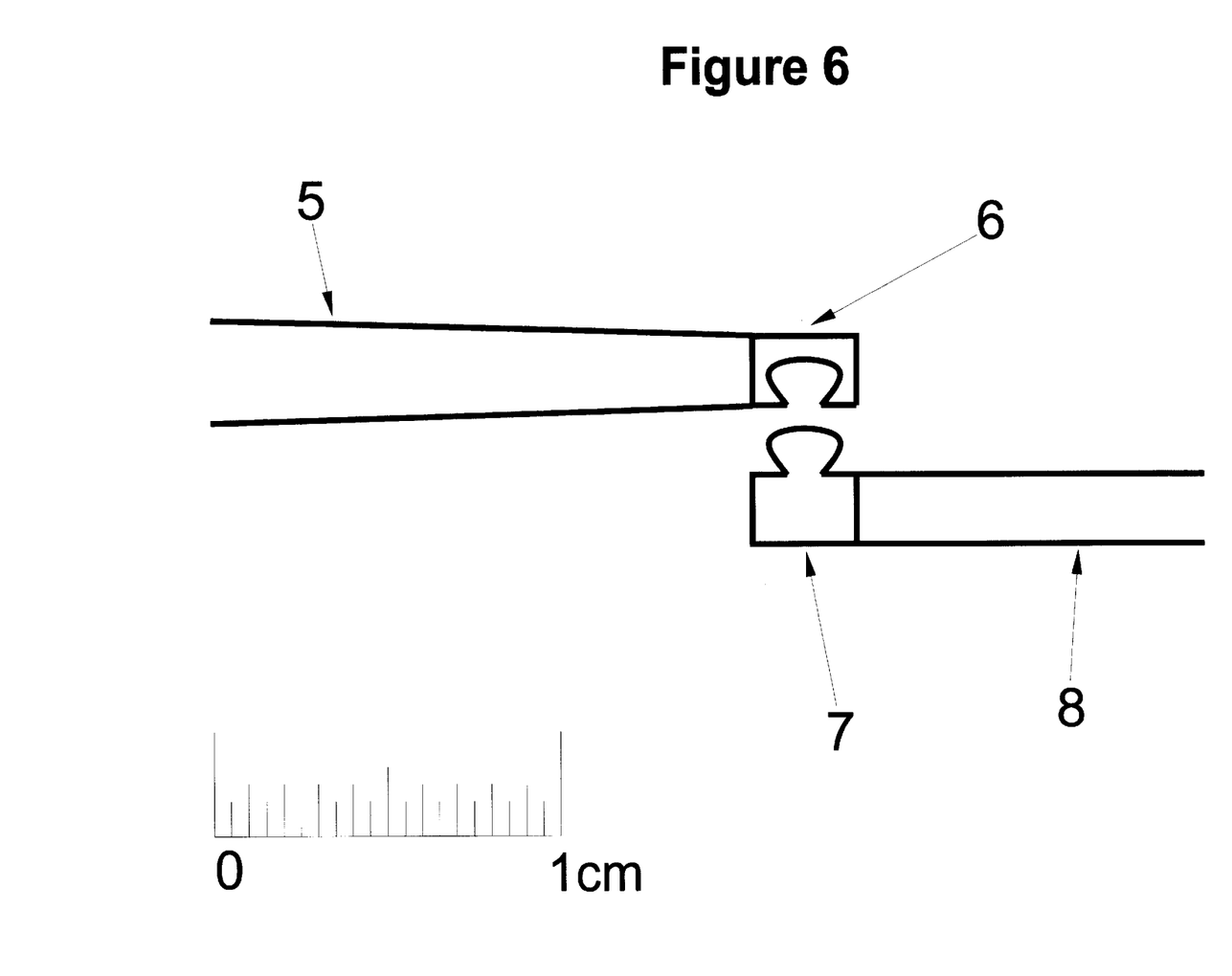
FIG. 6 illustrates the clip mechanism for attachment of the guides to the long hollow tubes.

The clips 7 are then clipped onto to the clips 6, which are attached to the tapered end 5 of the long hollow tubes 1. The whole stent is clipped on such that the curvature of the hollow tubes 1 is directed forwards. The fine guides 8 are then pulled out of the nose pulling with them the rest of the stent proper as depicted in FIG. 1. The transverse tube 2 then lies at the back of the nose blocked from further movement by the nasal septum. The tapered ends 5 and clips 6 lie outside the front of the nose.

Figure 7:
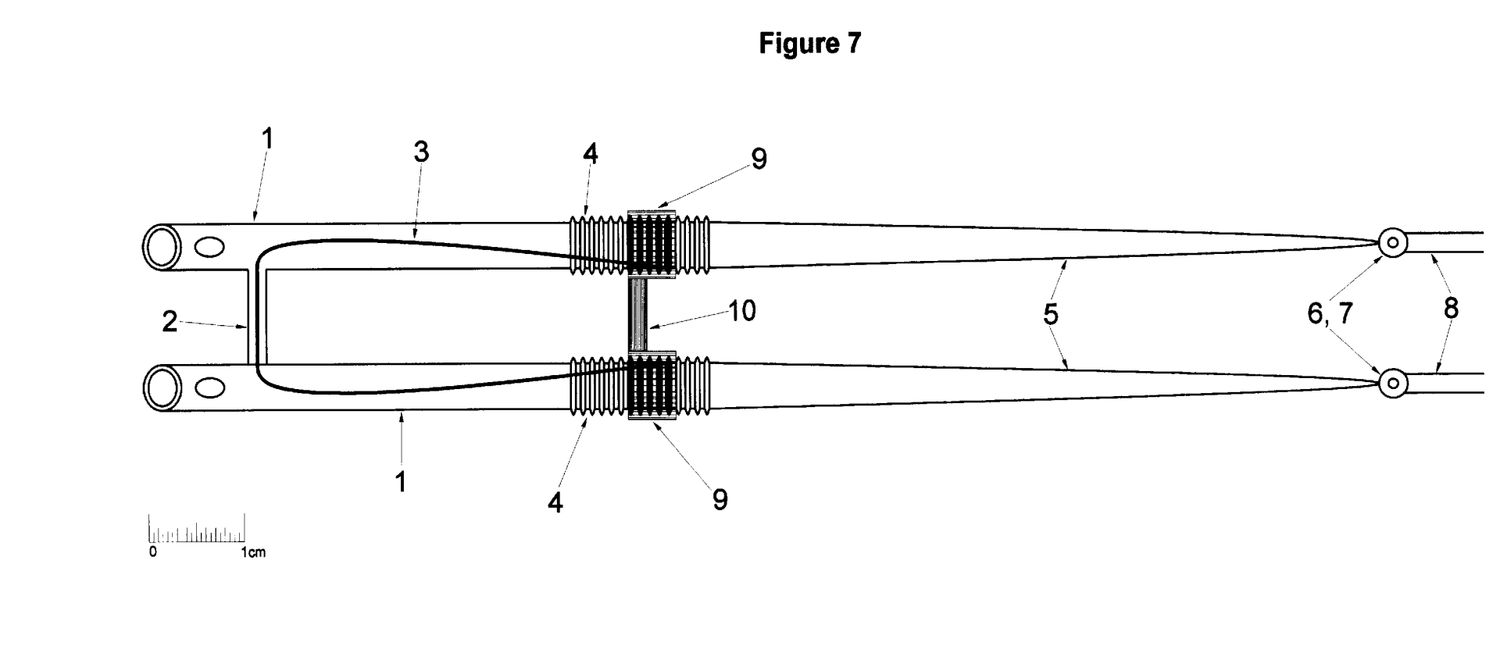
FIG. 7 shows the complete device, illustrating the short hollow tubes threaded over the long hollow tubes with the guides clipped to the tapered ends.
Figure 8:
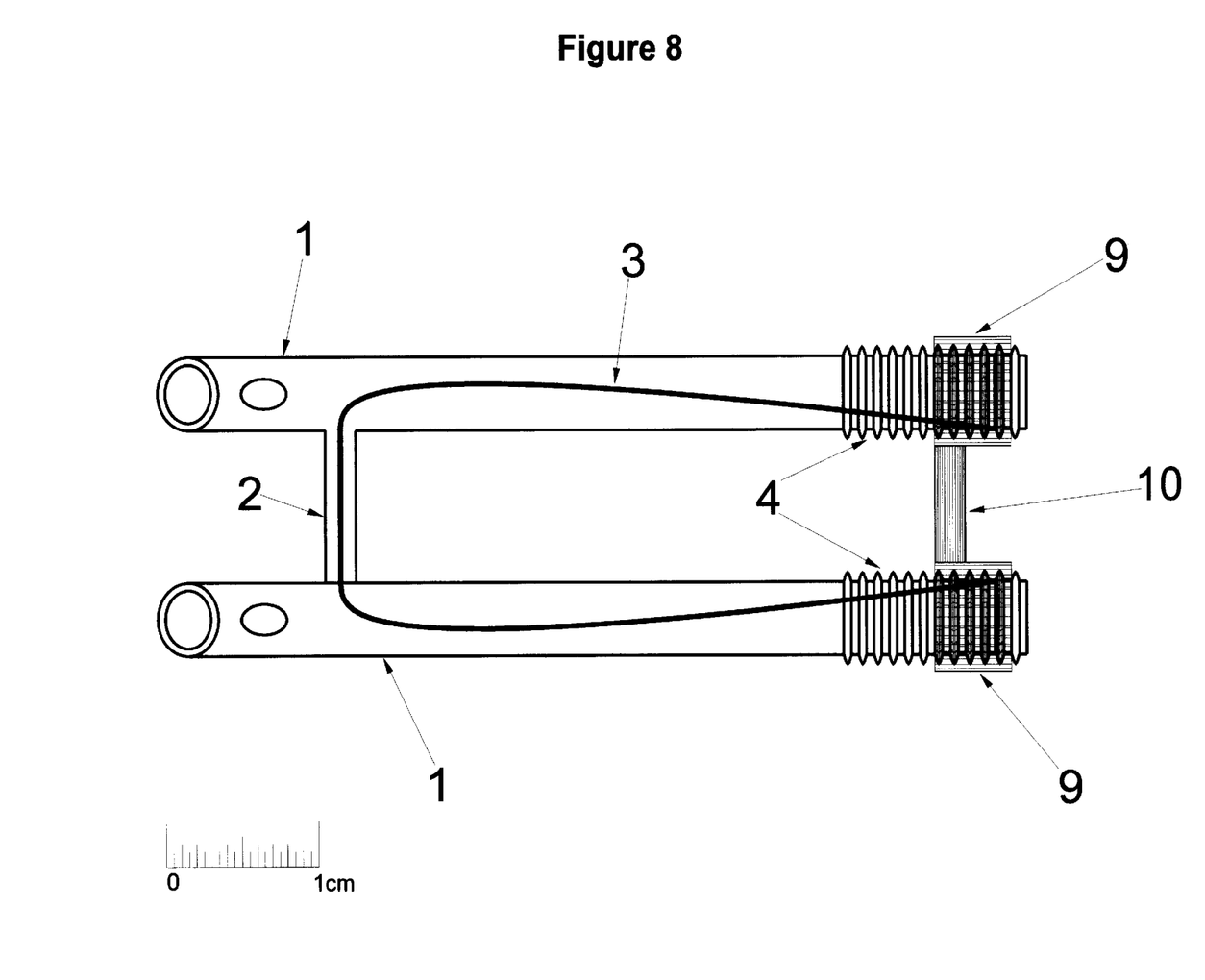
FIG. 8 shows the complete stent as left in the nose, after trimming off the excess tubing from the long hollow tubes.

The fine guides 8 are removed, and the short, grooved hollow tubes 9 connected by the transverse tube 10 are slipped over the tapered ends 5 and threaded through until engaged by the raised concentric ridges 4, as shown in FIG. 7. The placement of the short tubes 9 is adjustable using this mechanism, and adjustment is made for the patient such that the transverse tube 10 lies 0.5 cm outside the nose. The excess tubing is then trimmed off, leaving the stent as shown in FIG. 8.

After an appropriate period of time, the stents may be removed without general anaesthesia simply by cutting the thread in one of the long hollow tubes 1 below the level where the strong thread is attached. The flexible transverse tube 2 will now separate on one side, and collapse sufficiently to allow the whole stent to be removed from the nose.

What is claimed is:

1. A choanal atresia stent comprising:

two long hollow tubes, each of the two tubes having a distal end and a proximal end;

a first flexible transverse tube bridging the two long tubes at their proximal ends, the first flexible transverse tube being rigidly connected to only one of the long hollow tubes;

two short hollow tubes having an inner diameter larger than the outer diameter of the long hollow tubes so that the short tubes slide over the long hollow tubes;

a second transverse tube rigidly connecting the two short hollow tubes;

and a strong thread attached to each of the long hollow tubes and running from the inside of one of the long tubes, through the inside of the first transverse tube, to the inside of another of the long tubes so that the strong thread holds the two long tubes and the first transverse tube together.

2. The choanal atresia stent as claimed in claim 1, wherein each of the two long hollow tubes is tapered at its distal end to facilitate transnasal insertion of the long tubes into the choanal openings of a patient.

3. The choanal atresia stent as claimed in claim 1 or claim 2, further comprising long, fine and flexible guide wires attachable to distal ends of the long tubes.

4. The choanal atresia stent as claimed in claim 1 wherein each of the two long tubes includes a ridged outer surface and each of the short tubes include a ridged inner surface wherein the ridged inner surfaces of the two short tubes interfere with the ridged outer surfaces of the two long tubes to adjustably axially fix the short tubes over the long tubes.

* * * * *